United States Patent [19]

Adahan

[11] Patent Number: 4,726,745
[45] Date of Patent: Feb. 23, 1988

[54] PORTABLE FLUID PUMPING DEVICE

[76] Inventor: Carmeli Adahan, 1316/02, Ramot 03, Jerusalem 97 725, Israel

[21] Appl. No.: 833,195

[22] Filed: Feb. 27, 1986

[30] Foreign Application Priority Data

Mar. 8, 1985 [IL] Israel ........................................ 74546
Sep. 13, 1985 [IL] Israel ........................................ 76384

[51] Int. Cl.$^4$ ............................................. F04B 17/00
[52] U.S. Cl. .................................. 417/413; 417/423 R
[58] Field of Search ............... 417/413, 423 A, 423 T, 417/360; 604/317; 92/98 D

[56] References Cited

U.S. PATENT DOCUMENTS

| Re. 29,055 | 11/1976 | Wagner | 417/388 |
|---|---|---|---|
| 3,250,225 | 5/1966 | Taplin | 417/43 |
| 3,294,030 | 12/1966 | Fox | 92/98 D |
| 3,373,694 | 3/1968 | Taplin | 92/98 D |
| 3,452,751 | 7/1969 | Austin, Jr. | 417/182 |
| 3,776,666 | 12/1973 | Ludwig | 417/413 |
| 3,965,902 | 6/1976 | Reilly et al. | 604/320 |
| 4,256,109 | 3/1981 | Nichols | 604/320 |
| 4,482,301 | 11/1984 | Schlick | 417/413 |

FOREIGN PATENT DOCUMENTS 1014800 3/1950 France ........................... 417/413

Primary Examiner—Carlton R. Croyle
Assistant Examiner—Timothy S. Thorpe
Attorney, Agent, or Firm—Benjamin J. Barish

[57] ABSTRACT

A portable fluid pumping device, comprises a piston carried within a compartment by a rolling diaphragm and defining, on one side thereof, an expansible-contractible pumping chamber communicating with the inlet and outlet ports; a drive for the piston including an electric rotary motor and an eccentric bearing coupling the motor to the piston to reciprocate the piston upon the rotation of the motor; a flywheel coupled to the motor; and valves permitting fluid to enter the pumping chamber from the inlet port during the forward strokes of the piston, and to exit from the pumping chamber via the outlet port during the return strokes of the piston. The strokes of the piston are limited such that the volume of the pumping chamber in the contracted condition is more than 1/5 its volume in the expanded condition. In addition, the piston, drive, flywheel and valves are all arranged in a single assembly, the housing being partitioned to permit the quick introduction and removal of the single assembly for repair or maintenance purposes.

19 Claims, 4 Drawing Figures

FIG.1
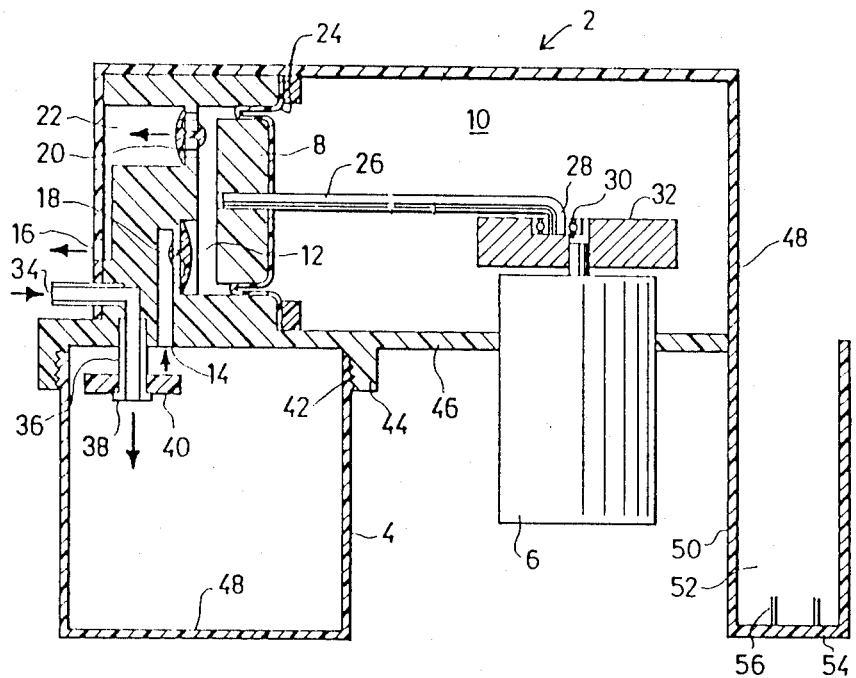
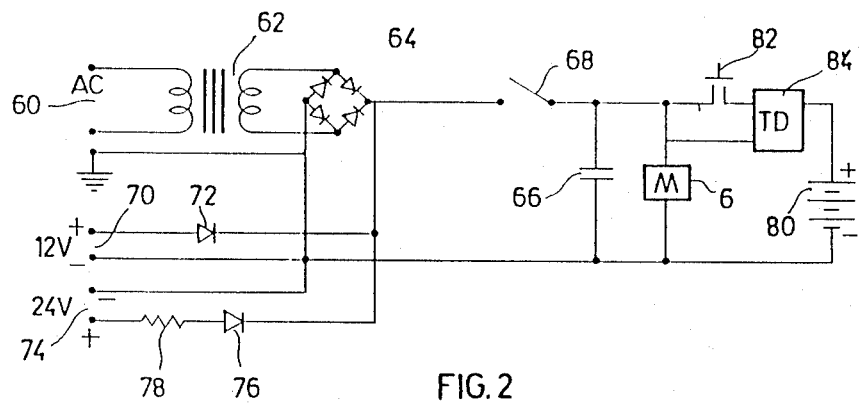
FIG.2

PORTABLE FLUID PUMPING DEVICE

BACKGROUND OF THE INVENTION

The present invention relates to pumping devices. The invention is particularly applicable to portable vacuum-producing machines, and is therefore described below with respect to this application.

Portable vacuum-producing machines are widely used as medical suction pumps, for example in drawing off waste fluids. A common type of medical suction pump now in use includes a cylinder and piston assembly with the piston reciprocated via a crank and piston rod. Reciprocation of the piston produces a vacuum within a sealed container for drawing waste liquids into the container.

Heretofore, medical suction pumps generally employed relatively large motors. This reduces the portability of the pumps and also precludes the use of small portable batteries for operating them. In addition, the known medical suction pumps are generally not capable of operating with several optional power sources, thus reducing their availability as an emergency stand-by medical aid. A further drawback in many of the existing medical suction pumps is the lack of a simple and reliable safety valve arrangement to terminate the suction when the container is full, and thereby to prevent the drawn liquids from entering the pump and contaminating or damaging it.

SUMMARY OF THE INVENTION

An object of the present invention is to provide a pumping device particularly useful as a portable vacuum-producing machine and having advantages in the above respects.

According to the present invention, there is provided a portable fluid pumping device comprising a housing having an internal compartment, a fluid inlet port, and a fluid outlet port; a piston carried within the compartment by a rolling diaphragm and defining, on one side thereof, an expansible-contractible pumping chamber communicating with the inlet and outlet ports; a drive for the piston including an electric rotary motor and an eccentric bearing coupling the motor to the piston to reciprocate the piston upon the rotation of the motor; a flywheel coupled to the rotary motor; and valve means permitting fluid to enter the pumping chamber from the inlet port during the forward strokes of the piston, and to exit from the pumping chamber via the outlet port during the return strokes of the piston.

According to an important feature in the preferred embodiments described below, the strokes of the piston are limited such that the volume of the pumping chamber in the contracted condition is more than 1/5 its volume in the expanded condition.

According to another described feature, the piston, drive, flywheel and valve means are all arranged in a single assembly, the housing being partitioned to permit the quick introduction and removal of the single assembly for repair or maintenance purposes.

Portable pumps constructed in accordance with the foregoing features provide a number of important advantages particularly when used as medical suction pumps. Thus, limiting the strokes of the piston such that the volume of the pumping chamber in its contracted condition is more than 1/5, preferably about ¼, its volume in the expanded condition, in combination with the flywheel, enables the pump to utilize relatively small motors while still producing relatively high suction, thereby increasing the portability of the pump and enabling it to use small portable batteries. In addition, the rolling diaphragm mounting for the piston permits free movement of the piston during its reciprocations, and thereby obviates the need for additional bearings, and also reduces friction. In addition, the arrangement permitting all the components to be introduced and removed quickly and conveniently as a single assembly from the housing, greatly facilitates repair and maintenance of the device.

BRIEF DESCRIPTION OF THE DRAWINGS

The invention is herein described, by way of example only, with reference to the accompanying drawings, wherein:

FIG. 1 is a sectional view illustrating one form of portable fluid pumping device constructed in accordance with the present invention;

FIG. 2 is a schematical diagram illustrating the circuit for operating the pumping device of FIG. 1;

DESCRIPTION OF PREFERRED EMBODIMENTS

The Construction of FIG. 1

Figure 3:
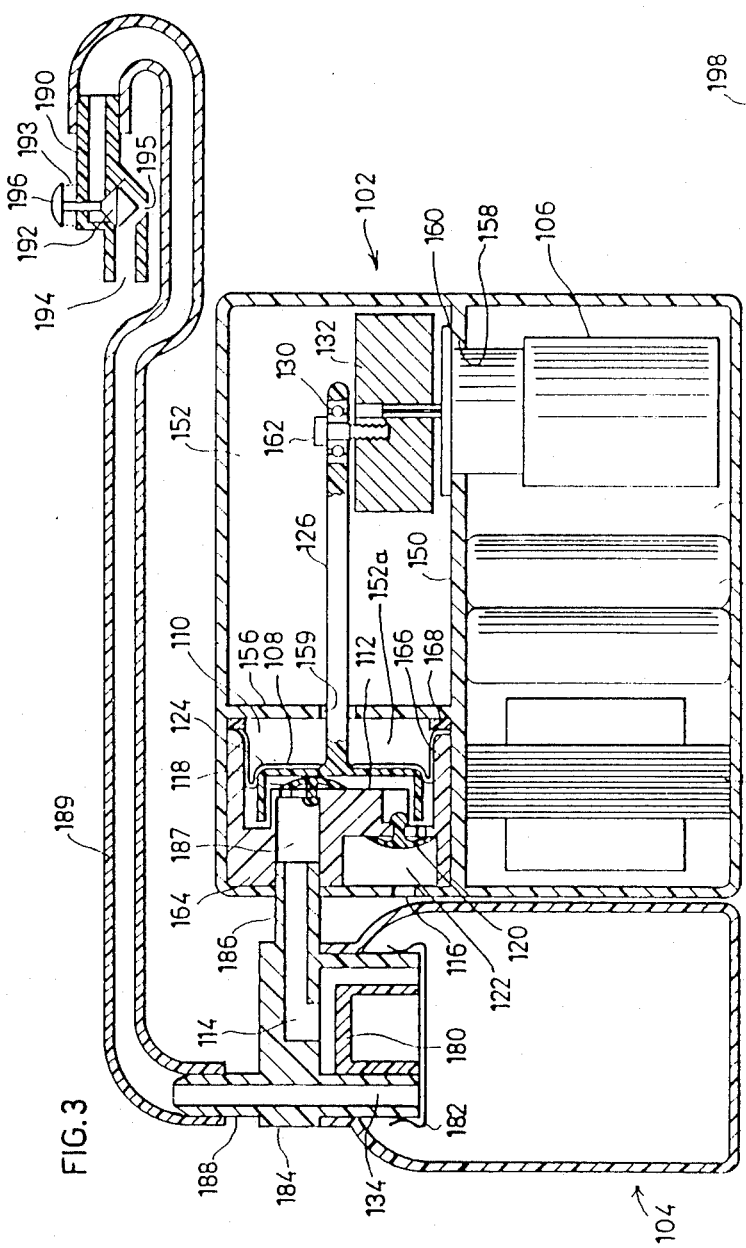
FIG. 3 illustrates an improved form of portable fluid pumping device constructed in accordance with the invention.

The pumping device illustrated in FIG. 1 is intended for use as a pumping suction pump for medical applications, such as for drawing off waste fluids into a container carried by the pump. The illustrated suction pump includes a housing 2, carrying a container 4 into which the liquids are drawn. The suction pump is operated by an electric motor 6 which reciprocates a piston 8 disposed within an internal compartment 10 of housing 2. Piston 8 defines, at one side of compartment 2, a pumping chamber 12 which communicates with the interior of container 4 via a bore 14 defining an inlet port to the pumping chamber. Housing 2 further includes an outlet port 16 also communicating with pumping chamber 12 for exhausting the air pumped out of that chamber.

Inlet port 14 communicates with pumping chamber 12 via a one-way valve 18 which permits air to enter the pumping chamber but not to exit therefrom; and outlet port 16 communicates with pumping chamber 12 via a one-way valve 20 which permits the air to exit from the pumping chamber but not to enter it. Housing 2 is formed with a cavity 22 between valve 20 and the outlet port 16 to muffle the air exausted from the pumping chamber via the latter port. Both valves 18 and 20 are preferably of the rubber-umbrella type, permitting air flow only in one direction.

Piston 8 is carried within housing 2 by a rolling diaphragm 24. The piston is coupled to motor 6 by a piston rod 26 secured at one end to the center of piston 8. Piston rod 26 is formed at its opposite end with a downturned extension 28 received within an eccentric bearing 30 carried by a flywheel 32 rotated by motor 6. Bearing 30 is disposed laterally of the axis of motor 6 and its flywheel 32 so that as the motor and flywheel rotate, bearing 28 reciprocates piston 8 by the oscillation of piston rod extension 28 on opposite sides of the rotary axis of the motor and flywheel.

The inlet into container 4, into which the liquid is drawn during the operation of the pump, includes an inlet tube 34 passing through a bore formed in housing 2 and entering the upper end of container 4. Inlet tube 34 is provided with an extension 36 depending into the interior of container 4, which extension terminates in an annular flange 38.

A floating sealing disc 40 is slidably supported on depending tube extension 36 to underlie outlet port 14 of container 4. Thus, extension 36 of inlet 34 supports the floating sealing disc 40 in suspension below outlet port 14 so as not to interfere with the exhaustion of the air from container 4 via port 14 and pumping chamber 12, but permits the sealing disc 40 to rise, with the rising level of liquid within container 4, to close port 14 when the container is full. The foregoing arrangement provides a simple and effective means for preventing liquid from container 4 flowing into pumping chamber 12 where it may contaminate or damage the pump.

Container 4 is formed with threads 42 at its upper end enabling it to be conveniently attached to a threaded annular flange 44 formed in the bottom wall 46 of housing 2. The bottom 48 of container 4 is flat. End wall 50 at the opposite end of housing 2 is extended downwardly to define a holder 52 for a battery (not shown). Holder 52 is also formed with a flat bottom 54. Thus, the pump can be stably supported on a horizontal surface by flat bottom 48 of container 4 and flat bottom 54 of battery holder 52. The battery holder further includes terminals 56 for connection to the batteries within the holder.

The operation of the pump illustrated in FIG. 1 will be apparent from the above description.

Energization of motor 6 rotates flywheel 32 and the eccentric bearing 30, the latter reciprocating piston rod 26 and piston 8. Rolling diaphragm 24 provides a sealed connection between piston 8 and housing 2, and permits free movement of the piston not only in the direction parallel to piston rod 26, but also in the direction transverse thereto as the downturned end 28 of the rod is oscillated in both directions by the rotation of eccentric bearing 30. The forward strokes of piston 8 cause pumping chamber 12 to be contracted, the air being expelled via one-way valve 20 and outlet 16; and the return strokes of the piston cause pumping chamber 12 to be expanded, drawing air from the interior of container 4 via the container outlet 14 and one-way valve 18.

The vacuum produced within container 4 draws liquid into the container from the source (not shown) to which the container inlet port 34 is connected. During this filling of the container with liquid, the floating sealing disc 40 is retained by flange 38 below the container outlet port 14 so that it does not interfere with the removal of the air from the container; but as the liquid level rises in the container, it causes sealing disc 40 to float upwardly until it closes the outlet port 14 when the container is substantially filled with liquid, to thereby prevent liquid from passing into the pumping chamber 12.

The illustrated arrangement limits the strokes of piston 8 such that the volume of the pumping chamber 12 in its contracted condition is more than 1/5, preferably about ¼, its volume in the expanded condition. This arrangement, together with the provision of flywheel 32, has been found to enable a small electric motor to be used and still obtain a relatively high level of vacuum without danger of stalling. For example, assuming the temperature of the air does not change during the reciprocations of piston 8, and assuming it is desired to obtain maximum vacuum level of 22 inches of mercury from a normal atmospheric pressure of 29.92 inches of mercury, the relationship $P_1V_1 = P_2V_2$ determines the volume of pumping chamber 12 in its contracted condition to be 0.265 the volume of the chamber in its expanded condition. Thus, the air in pumping chamber 12 acts to cushion the force applied to piston 8, while flywheel 32 stores energy during the expansion of the chamber and gives up energy during its contraction thereby preventing the motor from stalling.

The low energy requirement of motor 6 enables the suction pump to be constructed in the form of a small portable unit; it also enables it to be driven by a battery which can be supported within holder 52. In addition, the flat bottoms of container 4 and holder 52 enable the pump to be stably supported on a horizontal surface.

The Circuit of FIG. 2

The illustrated pump is thus particularly suited as an emergency stand-by medical aid which can be driven by any one of various types of power sources available at the site of use. FIG. 2 illustrates an electrical circuit that may be used in such an emergency stand-by unit.

Thus, as shown in FIG. 2, the pump includes a connector 60 for connecting the motor to an AC supply transformed via transformer 62, a rectifier 64, a filter capacitor 66, amd a switch 68.

The electrical circuit further includes a connector 70 for connecting the unit to a 12 volt DC source, such as an automobile battery, this circuit including a polarizing diode 72. The circuit of FIG. 2 further includes a connector 74 for connecting same to a 24-volt DC source, such as a 24 volt source battery, the voltage being applied via polarizing diode 76 and voltage-dropping resister 78 to reduce the 24 volts to 12 volts.

FIG. 2 illustrates a fourth alternative power supply in the form of a self-contained battery 80, located with holder 52 (FIG. 1); this battery is connected to drive motor 6 via a non-latching switch 82 and a time delay circuit 84, such that when switch 82 is depressed and then released, the motor is driven for a predetermined time interval, as fixed by time delay circuit 84, and then is automatically stopped.

The Construction of FIG. 3

The pumping device illustrated in FIG. 3 includes the same basic components as in FIG. 1, namely a housing 102 carrying a container 104 into which the liquids are drawn, and an electrical motor 106 which reciprocates a piston 108 disposed within an internal compartment 110. Piston 108 defines a pumping chamber 112 which communicates with the interior of container 104 via an inlet port 114, and exhausts the air from that chamber via an outlet port 116. The two ports 114, 116 communicate with pumping chamber 112 via one-way valves 118 and 120, respectively, the latter including a muffling cavity 122 corresponding to muffling cavity 22 in FIG. 1. Piston 108 is secured within the housing by a rolling diaphragm 124, and is coupled to motor 106 by a piston rod 126 coupled to an eccentric bearing 130 carried by a flywheel 132 rotated by motor 106, such that rotation of the motor and flywheel will reciprocate piston 8. The inlet into container 104, into which the liquid is drawn during the operation of the pump, includes a tube 134 serving as an inlet port entering the upper end of the container and provided with an extension depending into the interior of the container.

The pump illustrated in FIG. 3 includes the following improvements over that of FIG. 1.

Housing 102 is formed with a horizontal partition 150 dividing its interior into an upper compartment 152 and a lower compartment 154. The upper compartment 152 is in turn divided by a vertical partition 156 to form a sub-compartment 152a at one end (left end in FIG. 1). Horizontal partition 150 is formed with a wide slot 158 starting from one edge and terminating short of the opposite edge of the partition; and partition 156 is formed with a narrow slot 159 also starting from the corresponding edge as slot 158, and terminating short of the opposite edge.

Motor 106 is of cylindrical shape and is disposed within the lower compartment 154. The upper end of the motor has a diameter slightly less than the width of slot 158 so as to be received within that slot. The motor is formed with an annular flange 160 of larger diameter than the width of the slot so as to support the motor in a vertical position when received within the slot without the use of fasteners.

Flywheel 132 and eccentric bearing 130 are both disposed within the upper compartment 152. Piston rod 126 couples eccentric bearing 130 to piston 108 in compartment section 152a. The piston rod passes through slot 159 in partition 156 and is of smaller diameter that the width of the slot so that the piston rod can freely reciprocate with the rotation of motor 106. The end of piston rod 126 is coupled to eccentric bearing 130 by a threaded fastener 162.

The two one-wave valves 118 and 120 are supported by a block 164 also received within section 152a of the upper compartment 152. Block 164 is formed with a cavity cooperable with rolling diaphragm 124 of piston 108 to define the pumping chamber 112. The outer periphery of rolling diaphragm 124 is secured between the annular end 166 of block 164 and a retainer ring 168 interposed between the block and the vertical partition 156.

The lower compartment 154 includes, in addition to the motor 106, a set of batteries 170 for operating the pump, and a transformer 172 for operating the pump from the AC supply mains.

The foregoing construction permits the quick and simple assembly and disassembly of the main components for repair or maintenance purposes. Thus, the entire assembly, including eccentric bearing 130, piston rod 126, piston 108, block 164, diaphragm 124, and valves 118 and 120, all considered maintenance items, may be removed as an assembly by merely removing fastener 162 and sliding them out from slots 158 and 159 in partitions 150 and 156.

Another advantage in the described arrangement is the overflow protection valve for preventing liquid from container 104, if full, from entering the pumping chamber 112. In the arrangement illustrated in FIG. 3, this overflow valve is in the form of an inverted cup 180, e.g. made of hard plastic material, and retainer means, shown in FIG. 3 as a clip 182, for normally retaining the cup in alignment with, but spaced slightly below, the container outlet port 114. During the normal operation, cup 180 does not block the container outlet port 114, so as to permit the pumping chamber 108 to produce a suction within container 104, and thereby to draw liquid into the container via the container inlet port 134. However, when the quantity of the liquid drawn into container 104 increases to a level approaching that of the outlet port 114, cup 180 will float on the liquid until it closes the outlet port 114, thereby blocking the passage of the liquid to the pumping chamber 112.

Cup 180 produces an imperfect seal with respect to port 114, so that when the liquid level within container 104 recedes, the cup will drop back by gravity, thereby reopening port 114, and enabling continued operation of the pump, without requiring manual release.

Both the container inlet port 134 and outlet port 114 are formed in a fitting 184 received within the open mouth of container 104. Fitting 184 includes a nipple 186 frictionally received within a bore 187 formed in block 164 for attaching the fitting, and the container, to the pump housing 102.

Fitting 184 further includes a sleeve connector 188 adapted to receive one end of a flexible tube 189, of sufficient length so that the opposite end of the tube may be manipulated at the location where suction is desired. This opposite end of tube 189 is adapted to receive another fitting 190 carrying a valve assembly including a valve member 192 normally urged by spring 193 to seal flexible tube 189 from the atmosphere. Fitting 190 further includes a suction tip 194 formed with a vent, 195 leading to the atmosphere and underlying valve member 192. A push-button 196, when depressed, causes valve member 192 to close vent 195 and to connect the suction tip 194 to tube 189 so as to transmit to the suction tip the suction produced by the operation of the pump.

Figure 4:
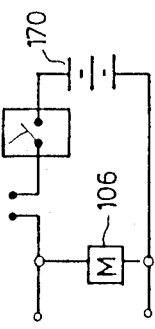
FIG. 4 illustrates a modification in the electrical circuit for operating the pumping device of FIG. 3.

In order to minimize the consumption of power, particularly when the pump is battery operated, a vacuum switch may be included to automatically terminate the operation of the pump when a required vacuum is produced. This modification is illustrated in FIG. 4, wherein it will be seen that vacuum switch 198 is provided in series with the motor 106 and battery 170, the vacuum being effective to disconnect the motor from the battery when a predetermined vacuum has been produced.

While the invention has been described for producing a suction, i.e., a negative pressure, it will be appreciated that it could also advantageously be used for producing a positive pressure. Many other variations, modifications and applications of the invention will be apparent.

I claim:

1. A portable fluid pumping device, comprising:
   a housing having an internal compartment, a fluid inlet port, and a fluid outlet port;
   a piston carried within said compartment by a rolling diaphragm and defining, on one side thereof, an expansible-contractible pumping chamber communicating with said inlet and outlet ports;
   a drive for said piston including an electric rotary motor, an eccentric bearing rotated by the motor, and a piston rod coupling the eccentric bearing to the piston to reciprocate the piston upon the rotation of the motor;
   a flywheel coupled to said rotary motor;
   valve means permitting fluid to enter said pumping chamber from said inlet port during the forward strokes of said piston, and to exit from the pumping chamber via said outlet port during the return strokes of said piston;
   a partition in said housing and formed with a slot extending from one edge thereof;
   and means securing together said piston, piston rod, rolling diaphragm, flywheel, eccentric bearing and valve means such that they are all insertable and removable as a unitary assembly, with the valve means, piston and rolling diaphragm received on one side of the partition, said flywheel and eccentric bearing received on the other side of the partition, and said piston rod passing through said slot in the partition so that the slot accommodates the piston rod during its reciprocations.

2. The pumping device according to claim 1, wherein the strokes of said piston such that the volume of the pumping chamber in the contracted condition is more than 1/5 its volume in the expanded condition.

3. The pumping device according to claim 1, wherein said partition extends along the vertical axis of the housing in the normal use of the device, and said housing includes a further partition extending along the horizontal axis in the normal use of the device and defining an upper compartment containing said vertically-extending partition and a lower compartment, said horizontally-extending partition being formed with a second slot extending from said one edge of the housing, said motor being formed with an end flange of larger diameter than the width of the said second slot, thereby permitting the motor, upon the insertion of said unitary assembly into the housing, to be received in said lower compartment, with said piston, piston rod, eccentric bearing, and flywheel disposed in said upper compartment, and with said end flange removably supporting the motor from said horizontally-extending partition.

4. The pumping device according to claim 3, wherein said piston rod is coupled to said eccentric bearing by a removable fastener, which, when removed, permits said motor, piston, piston rod, rolling diaphragm, valve means, eccentric bearing and flywheel to be slid out of the housing as a unitary assembly.

5. The pumping device according to claim 1, wherein said housing further includes a container having an inlet port for a liquid, and an outlet port communicating with said inlet port of the pumping chamber such that the operation of the motor produces a suction drawing liquid into said container from its inlet port.

6. The pumping device according to claim 1, wherein said valve means are carried by a block slidably received in said housing between said partition and an end wall of the housing, said block securing the outer periphery of the rolling diaphgram between it and said partition.

7. The pumping device according to claim 6, wherein said block is formed with an inlet port controlled by a first valve member and communicating with the housing inlet port, an outlet port controlled by a second valve member and communicating with the housing outlet port, and a cavity between the block outlet port and the housing outlet port to muffle the air exhausted from the pumping chamber.

8. The pumping device according to claim 7, wherein said first and second valve members are umbrella-type valves.

9. The pumping device according to claim 5, further including a flexible tube connected at one end to said container inlet port, said flexible tube including a push-button valve which normally closes the opposite end of said tube but which, when depressed, opens said opposite end to draw liquid therethrough and into said container by the vacuum produced in said container.

10. A portable fluid pumping device, comprising:
a housing having an internal compartment, a fluid inlet port, and a fluid outlet port;
a piston carried within said compartment by a rolling diaphragm and defining, on one side thereof, an expansible-contractible pumping chamber communicating with said inlet and outlet ports;
a drive for said piston including an electric rotary motor, an eccentric bearing rotated by the motor, and a piston rod coupling the eccentric bearing to the piston to reciprocate the piston upon the rotation of the motor;
a flywheel coupled to said rotary motor;
valve means permitting fluid to enter said pumping chamber from said inlet port during the forward strokes of said piston, and to exit from the pumping chamber via said outlet port during the return strokes of said piston;
and means limiting the strokes of said piston such that the volume of the pumping chamber in the contracted condition is more than 1/5 its volume in the expanded condition.

11. The pumping device according to claim 10, further including a partition formed with a slot extending from one edge thereof; and means securing together said piston, piston rod, rolling diaphragm, eccentric bearing, flywheel and valve means such that they are all insertable and removable as a unitary assembly with the valve means, said piston, valve means and rolling diaphragm being received on one side of the partition, said flywheel and eccentric bearing received on the other side of the partition, and said piston rod passing through said slot in the partition so that the slot accommodates the piston rod during its reciprocations.

12. The pumping device according to claim 11, wherein said partition extends along the vertical axis of the housing in the normal use of the device, and said housing includes a further partition extending along the horizontal axis in the normal use of the device and defining an upper compartment containing said vertically-extending partition and a lower compartment, said horizontally-extending partition being formed with a second slot extending from said one edge of the housing, said motor being formed with an end flange of larger diameter than the width of the said second slot, thereby permitting the motor, upon the insertion of said unitary assembly into the housing, to be received in said lower compartment, with said piston, piston rod, eccentric bearing, and flywheel disposed in said upper compartment, and with said end flange removably supporting the motor from said horizontally-extending partition.

13. The pumping device according to claim 12, wherein said piston rod is coupled to said eccentric bearing by a removable fastener, which, when removed, permits said motor, piston, piston rod, rolling diaphragm, valve means, eccentric bearing and flywheel to be slid out of the housing as a unitary assembly.

14. The pumping device according to claim 10, wherein said housing further includes a container having an inlet port for a liquid, and an outlet port communicating with said inlet port of the pumping chamber such that the operation of the motor produces a suction drawing liquid into said container from its inlet port.

15. A portable fluid pumping device, comprising:
a housing having an internal compartment, a fluid inlet port, and a fluid outlet port;
a piston carried within said compartment by a rolling diaphragm and defining, on one side thereof, an expansible-contractible pumping chamber communicating with said inlet and outlet ports;
a drive for said piston including an electric rotary motor, an eccentric bearing rotated by the motor, and a piston coupling the eccentric bearing to the piston to reciprocate the piston upon the rotation of the motor;

a flywheel coupled to said rotary motor;

valve means permitting fluid to enter said pumping chamber from said inlet port during the forward strokes of said piston, and to exit from the pumping chamber via said outlet port during the return strokes of said piston;

and a partition in said housing;

said valve means being carried by a block slidably received in said housing between said partition and an end wall of the housing, said block securing the outer periphery of the rolling diaphragm between it and said partition.

16. The pumping device according to claim 15, wherein said block is formed with an inlet port controlled by a first valve member and communicating with the housing inlet port, an outlet port controlled by a second valve member and communicating with the housing outlet port, and a cavity between the block outlet port and the housing outlet port to muffle the air exhausted from the pumping chamber.

17. The pumping device according to claim 16, wherein said first and second valve members are umbrella-type valves.

18. The pumping device according to claim 15, wherein the strokes of said piston are limited such that the volume of the pumping chamber in the contracted condition is more than 1/5 its volume in the expanded condition.

19. The pumping device according to claim 15, wherein said housing further includes a container having an inlet port for a liquid, and an outlet port communicating with said inlet port of the pumping chamber such that the operation of the motor produces a suction drawing liquid into said container from its inlet port.

* * * * *

UNITED STATES PATENT AND TRADEMARK OFFICE
CERTIFICATE OF CORRECTION

PATENT NO. : 4,726,745

DATED : February 23, 1988

INVENTOR(S) : Carmeli Adahan

It is certified that error appears in the above-identified patent and that said Letters Patent is hereby corrected as shown below:

Column 7 (Claim 2), line 7, cancel "wherein".

Column 7 (Claim 2), line 8, add at beginning of line -- further including means limiting --.

Signed and Sealed this

Fourth Day of April, 1989

Attest:

DONALD J. QUIGG

Attesting Officer

Commissioner of Patents and Trademarks